United States Patent [19]

Etlinger et al.

[11] Patent Number: 6,015,837
[45] Date of Patent: Jan. 18, 2000

[54] METHOD FOR TREATING SCOLIOSIS WITH β2-ADRENOCEPTOR AGONISTS

[75] Inventors: Joseph D. Etlinger, Mt. Kisco; Richard J. Zeman, New York, both of N.Y.

[73] Assignee: New York Medical College, Valhalla, N.Y.

[21] Appl. No.: 08/920,018

[22] Filed: Aug. 26, 1997

Related U.S. Application Data

[60] Provisional application No. 60/025,147, Aug. 29, 1996.
[51] Int. Cl.⁷ .......................... A01N 33/02; A61K 31/135
[52] U.S. Cl. .......................... 514/653; 514/307; 514/311; 514/315; 514/602; 514/603; 514/604; 514/646; 514/649; 514/654
[58] Field of Search ..................................... 514/653, 307, 514/311, 315, 602, 603, 604, 646, 649, 654

[56] References Cited

U.S. PATENT DOCUMENTS 4,830,009   5/1989   Schmitt et al. ........................... 607/43

OTHER PUBLICATIONS

Chemical Abstracts (I) vol. 115: 174604h (Zeman et al), 1991.
Chemical Abstracts (II) vol. 86: 101038z (Malatray et al), 1977.
Chemical Abstracts (III) vol. 91: 49640b (Salvehi et al), 1979.
Chemical Abstracts (IV) vol. 105:184601n (Grover et al), 1986.

*Primary Examiner*—Frederick Krass
*Attorney, Agent, or Firm*—Skadden, Arps, Slate, Meagher & Flom LLP; Evelyn M. Sommer

[57] ABSTRACT

A method of treating scoliosis by adminstering $\beta_2$ adrenergic agonists in amounts sufficient to correct the condition.

12 Claims, 4 Drawing Sheets

PRECURSORS

PHENYLALANINE

TYROSINE

DOPA

METABOLITES

METHOXYTYRAMINE

NORMETANEPHRINE

METANEPHRINE

AGONISTS

DOPAMINE

EPINEPHRINE

ISOPROTERENOL

METAPROTERENOL

CLENBUTEROL

CIMATEROL

FIG. 3B

METHOD FOR TREATING SCOLIOSIS WITH β2-ADRENOCEPTOR AGONISTS

This application claims priority to U.S. Provisional Patent Application Ser. No. 60/025,147, filed Aug. 29, 1996.

BACKGROUND OF THE INVENTION

Scoliosis, or lateral curvature of the spine, can occur as congenital type scoliosis or as familial or idiopathic type scoliosis (D'Ambrosia 1986), can result from the neuromuscular effects of a spinal cord injury (Dearolf 1990), or can result from illnesses causing neuromuscular weakness such as muscular dystrophy (Galasko 1933, Beals 1973). Whatever the cause, scoliosis is a major complication which hampers rehabilitation by impairing the body's skeletal support, and which compromises vital functions such as breathing and circulation by altering thoracic and abdominal geometry (D'Ambrosia 1986).

The lateral curvature of the spine in scoliosis is thought to be a consequence of insufficient and asymmetrical loading of the vertebrae. This is why scoliosis is highly prevalent under conditions that cause neuromuscular weakness. In fact mathematical modelling of the effects of weakened muscle contractility on vertebral loading can produce curves that are virtually identical to those observed in scoliosis patients (Schultz 1981, Takashima 1979, Ghista 1988).

Idiopathic scoliosis is the most common form (70%) of scoliosis. Although the specific mechanism is unknown (D'Ambrosia 1986), it is probable that neuromuscular abnormalities are also involved in idiopathic scoliosis (Maguire 1993, Kennelly 1993). This accounts for the aberrant prolongation of the spinal reflex activity for maintenance of posture observed in patients with idiopathic scoliosis (Maguire 1993). This reflex activity could not be ascribed to spinal curvature itself, since normal activity was measured in patients with similar but nonidiopathic curves. Also, the cross-sectional areas of paraspinal muscles, which support the spine, are unequal in idiopathic scoliosis (Kennelly 1993).

Because of the negative health effects and discomfort associated with scoliosis, it is important to reduce or eliminate scoliosis in an affected person. The standard practice is to try to correct the asymmetrical loading of the spine in scoliosis by braces which are surgically implanted or externally applied (D'Ambrosia 1986). Repeated electrical stimulation of weakened muscles has also been tried as a countermeasure (Schultz 1981). However, these modalities are invasive and cumbersome. Moreover, it is necessary to precisely determine the anatomical location at which to apply these corrective forces. If the forces are not correctly applied, this can actually worsen the scoliotic condition. Clearly alternatives, particularly of a pharmacological nature, are desirable. However, a difficulty in using pharmacological approaches is targeting the comparatively weaker musculature on the side of the spine which is convex. Unlike a systemically administered pharmaceutical, braces and electrical stimulation can, although with difficulty, be targeted to the specific region of treatment. In contrast, a systemically administered pharmaceutical would be expected to affect both the weaker and stronger sides equally or even favor the stronger side (Zeman II 1991), thus not to correct the asymmetry.

$\beta_2$-adrenoceptor agonists ($\beta_2$-agonists) are a class of compounds which have the same effect as the hormone epinephrine (adrenaline) binding to the adrenergic receptors found in smooth and skeletal muscle, nervous tissue, and bronchioles. Unlike epinephrine, $\beta_2$-agonists activate primarily the $\beta_2$ receptor, not the $\beta_1$ receptor, thus avoiding some of the "fight-or-flight" effects of epinephrine, such as increased heartrate. Because of their effect on bronchioles, $\beta_2$-agonists are well known for treating asthma.

It is also known that $\beta_2$-agonists can alter bone mass, probably due to increasing muscle tone (Zeman II 1991). $\beta_2$-agonists treatment also reduces loss of muscle mass and contractility in dystrophic (mdx) muscle whose fiber regeneration has been blocked (Zeman II 1994). Studies with the $\beta_2$-agonist clenbuterol show that $\beta_2$-agonists can partially oppose reductions in bone mineralization and muscle contractility that occur in response to surgical denervation (Zeman I 1987, Zeman II 1991, Agbenyega 1990). Clenbuterol has been used to increase strength in orthopedic patients following knee surgery (Maltin 1993). However, until the present invention, it has not been shown that these effects of $\beta_2$-agonists would have any applicability to spinal musculature, even less in the special situation of scoliosis where asymmetry is a problem.

SUMMARY OF THE INVENTION

We have now shown that $\beta_2$-agonists such as clenbuterol may be properly administered in scoliosis to oppose vertebral unloading due to neuromuscular weakness. In contrast to our expectations, loading of the spine becomes more equal—i.e. the lateral displacement of the spine is corrected, treating the scoliosis. Thus it is possible to administer these agents systemically without direction to a specific anatomical site.

Thus, it is an object of this invention to provide a method for treating scoliosis by administering to a patient with scoliosis an amount of a $\beta_2$ adrenergic agonist effective to reduce the scoliosis. Scoliosis induced by muscular dystrophy is particularly amenable to this treatment.

Also part of this invention is a composition including a $\beta_2$ adrenergic agonist and a $\beta_1$ antagonist or mixed $\beta$ blocker. A method of adminstering this composition to a patient with scoliosis in an amount effective to reduce the scoliosis and to prevent side effects caused by co-stimulation of the $\beta_1$ receptor is also an object of this invention.

DETAILED DESCRIPTION OF THE INVENTION

We have demonstrated for the first time that $\beta_2$-agonists are an effective treatment for scoliosis. Accordingly, this invention is directed to a method of treating scoliosis by using $\beta_2$-agonists to reduce or eliminate the condition. Reduce in this context includes reduction to the point that the scoliosis is completely eliminated, and also includes all levels of amelioration of the condition short of complete elimination.

A. $\beta$ Adrenergic Receptor Compounds

1. $\beta_2$-Agonists $\beta_2$-agonists are compounds which stimulate the $\beta_2$ adrenergic receptors found on skeletal and smooth muscles. Any compound which has this activity is a $\beta_2$-agonist within the meaning of this invention.

To determine whether a compound for use in this invention has $\beta_2$-agonist activity, assays known to a skilled person may be performed. One such assay is exposing preparations of artery, skeletal muscle, or bronchiole tissue to the compound and measuring the changes in the amount of muscle force developed, using methods known in the art (see for example Bowman).

Known $\beta_2$-agonists include the known compounds albuterol, salmeterol, ractopamine, salbutamol, cimaterol, BRL-47672, terbutaline, fenoterol, metaproterenol, isopraline, MJ-9184-1, trimetoquinol, tetrahydropapaveroline, soterenol, salmefamol, rimiterol, QH-25, isoetharine, R-804, orciprenaline, quinterenol, sulfonterol, dobutamine, and isoproterenol and their salts. Preferred $\beta_2$-agonist are albuterol, salmeterol, ractopamine, salbutamol, cimaterol, BRL-47672, terbutaline, fenoterol, metaproterenol, and isopraline. A particularly preferred $\beta_2$-agonist is clenbuterol. These compounds may be used as racemates or enantiomers.

Figure 3A:
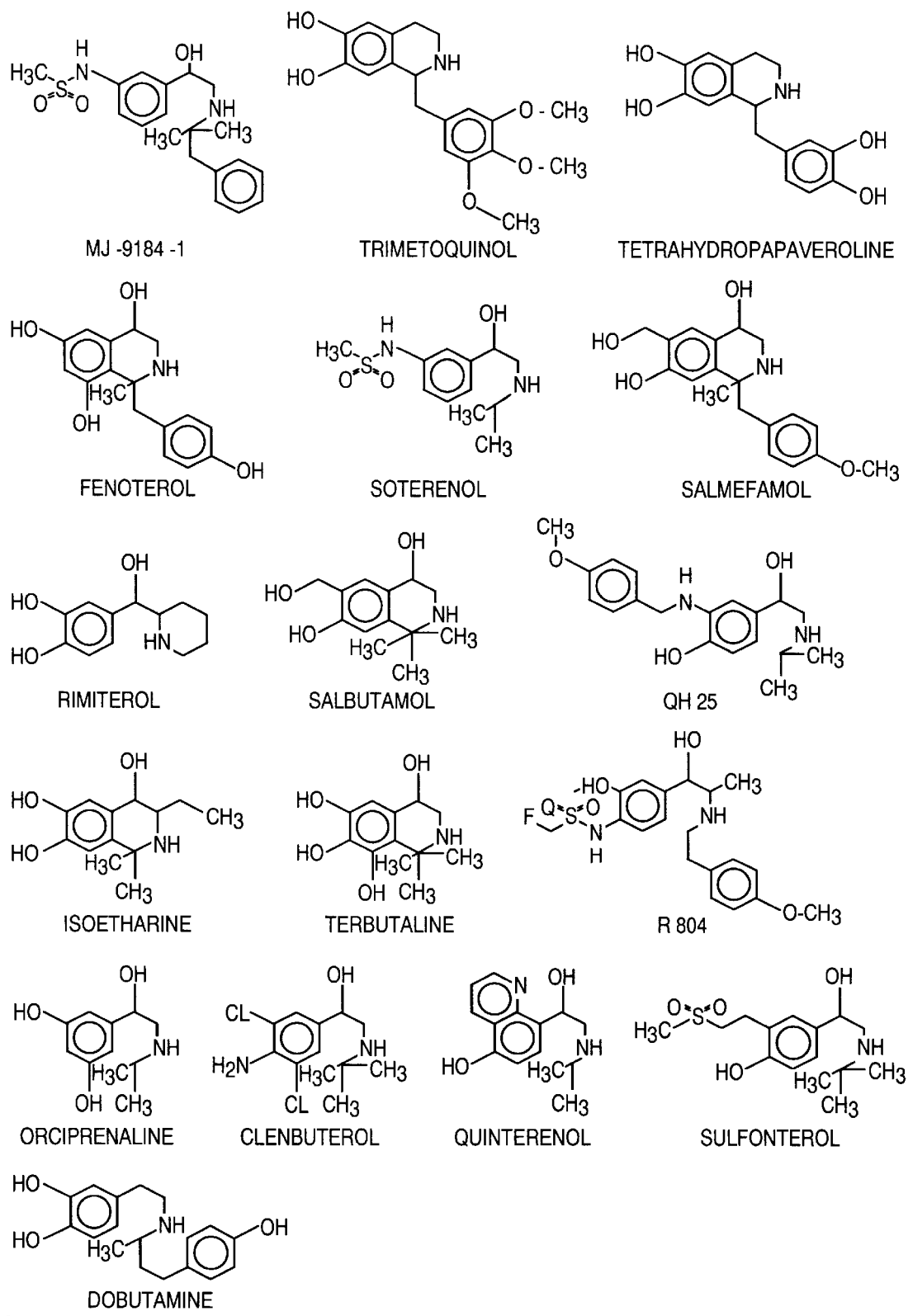
FIG. 3. Chemical structures of $\beta_2$ agonists (and precursors).

These known compounds are based on the chemical structure of epinephrine. As can be seen from the structures depicted in FIG. 3, these $\beta_2$-agonists are modified catecholamines having the structural features common to this group, specifically a terminal phenyl ring substituted with an aliphatic chain including an amine and a hydroxyl group. The known $\beta_2$-agonists useful in this invention may be in the form of racemic mixtures or in the form of isolated enantiomers.

The above-described $\beta_2$-agonists of this invention are known and can be obtained by the skilled person by conventional methods of chemical synthesis from readily available reagents (see FIG. 3, including precursors) Many of these compounds are also commercially available from chemical suppliers (see the Merck Index). For example, clenbuterol may be obtained as described in U.S. Pat. No. 3,536,712 (incorporated herein by reference). Clenbuterol is also commercially available from Boehringer Ingelheim and Sigma Chemicals. Enantiomers of $\beta_2$-agonists such as clenbutarol may be obtained by methods known to the skilled chemist and are contemplated by this invention.

Of course, there may be other known or presently unknown compounds having $\beta_2$ agonist activity which may or may not be chemically similar to those described above, and all such compounds and their use would be within the scope of the present invention.

2. $\beta_1$-Antagonists, Mixed $\beta$ Blockers:

$\beta_1$-antagonists are compounds which prevent stimulation of $\beta_1$ adrenergic receptors found on skeletal and smooth muscles. These receptors are responsible for causing increased heartrate and other well-known effects of the "fight-or-flight" adrenergic response. Any compound which has this activity is a $\beta_1$-antagonist within the meaning of this invention. Mixed $\beta$ blockers prevent stimulation of both $\beta_1$ and $\beta_2$ adrenergic receptors. Any compound which has this activity is a mixed $\beta$ blocker within the meaning of this invention.

To determine whether a compound for use in this invention has antagonistic activity, assays known to a skilled person may be performed. For example with regard to $\beta_2$ antagonistic activity, the assay described above for measuring $\beta_2$ agonistic activity may be used, if a compound reduces or blocks the activity of an agonist, then it has antagonistic activity. With regard to $\beta_1$ activity, assays for this are well known. For example, an antagonist will decrease the heartrate of an experimental animal whose heartrate has been stimulated. A similar assay may be performed with blood pressure, which will be decreased by an antagonist. A mixed $\beta$ blocker will have both activities. An active compound may be a racemate or enantiomer or in salt form.

A number of specific $\beta_1$-antagonists and mixed $\beta$ blockers are well known in the art. See for example the Physician's Desk Reference, 51st ed. 1997 (PDR). Exemplary $\beta_1$ antagonists include CGP 20712 (Sillence 1995), and atenolol and metoprolol (PDR pp.2963, 560, Merck Index). An example of a mixed $\beta$ blocker is propranolol (PDR p. 2834, Merck Index).

The known $\beta_1$-antagonists and mixed $\beta$ blockers which fall within the scope of this invention are known and can be obtained by the skilled person by conventional methods of chemical synthesis from readily available reagents. Many of these compounds are also commercially available from chemical suppliers B. Scoliosis As noted above, scoliosis is a condition where the spine is curved laterally due to asymmetric loading of the vertebrae caused primarily by weakening of muscles supporting one side of the spine. The muscle weakness is ordinarily caused by reduced innervation of the affected muscles. The condition may be developed as result of a systemic neuromuscular disease such as muscular dystrophy or may be the result of an injury. The condition may also be congenital or familial. Since scoliosis is a result of asymmetric loading of the spine, it is surprising that the treatment of this invention may be used systemically and does not require a means to target the treatment modality to the affected area.

Scoliosis may be readily detected by physical examination or radiogram (x-ray) (see FIG. 2). Spinal curvature (i.e. vertebral deviation) is assessed by methods known to skilled persons. Medical practitioners commonly determine a Cobb angle to assess degree of scoliosis by measuring radiograms (see D'Ambrosia 1986). Cobb angles are measured on radiograms by drawing a line along the outermost vertebrae of the spinal curve, drawing lines parallel to the vertebrae, and measuring the angle between the lines. Thus practitioners are well able to assess the efficacy and progress of scoliosis treatment by monitoring the degree of spinal curvature in their patients.

Scoliosis is a common result of muscular dystrophy and other known neuromuscular conditions and reduction of scoliosis in such diseases by adminstration of $\beta_2$-agonist is an object of this invention.

C. Method of Treatment

The method of this invention provides for administration of a $\beta_2$ adrenergic agonist to a patient with scoliosis in an amount effective to correct the displacement of the patient's spinal column sufficiently to reduce the scoliosis. Reduction of scoliosis in this context is intended to include elimination, i.e. reduction to the point at which no scoliosis remains; it is also intended to include less dramatic degrees of improvement.

As discussed above, any compound having the activity of a $\beta_2$ agonist is useful in this invention. Particular $\beta_2$ agonists are albuterol, salmeterol, ractopamine, salbutamol, cimateril, BRL-47672, terbutaline, fenoterol, metaproterenol, isopraline, MJ-9184-1, trimetoquinol, tetrahydropapaveroline, soterenol, salmefamol, rimiterol, QH-25, isoetharine, R-804, ocripraline, quinterenol, sulfonterol, dobutamine, and isoproterenol. Preferred $\beta_2$ agonists are albuterol, salmeterol, ractopamine, salbutamol, cimateril, BRL-47672, terbutaline, fenoterol, metaproterenol, and isopraline. A particularly preferred $\beta_2$ agonist is clenbuterol (see FIG. 3 for structures). One or more $\beta_2$ agonists may be administered together, either simultaneously or at different times as part of the same treatment regimen. In this context, doses may be provided separately or combined in a single pharmaceutical composition.

An effective amount of $\beta_2$ agonist is an amount which significantly reduces scoliosis. This is readily established by a skilled practitioner based on before and after comparisons of the patient's condition using any known means of evaluating scoliosis. Examples of such means are physical examination, radiograms (x-rays), and Cobb angles as discussed above. Thus the skilled practitioner can administer a minimal starting dose of $\beta_2$ agonist, such as clenbuterol, to a patient and monitor the patient's spinal column. If improvement is noted then the same dose can be repeated. If not, the dose can be increased until improvement occurs, then that effective dose can be used for further treatment. Once the scoliosis is sufficiently ameliorated, the practitioner can determine whether to discontinue the treatment, or possibly to continue on a maintenance or prophylactic basis.

Determination of a minimal dose for hormone agonists such as those of this invention is known to a skilled practitioner. $\beta_2$ agonists such as clenbuterol are known as asthma medications. In addition, clenbuterol in particular is known to be a long lasting medication which is effective in low and high doses. The other $\beta_2$ agonists which are not long lasting would be more effective at higher or more frequent doses.

Specific dosage regimens for $\beta_2$ agonists in the method of this invention are from about 0.5 to about 1000.0 $\mu$g/kg/day. A range of from about 10.0 to about 100.0 $\mu$g/day is particularly effective, and about 40 $\mu$g/day is most effective. Thus for example clenbuterol may be administered in doses of from about 0.5 to about 1000.0 $\mu$g/kg/day, and in particular from about 10.0 to about 100.0 $\mu$g/day, preferably about 40 $\mu$g/day. The word "about" in this context includes a range above and below the numbers provided, as would be considered reasonable by a skilled practitioner. If more than one $\beta_2$ agonist is administered in one dose, then the dosages of each should be adjusted (downward) accordingly.

Pharmaceutical compositions containing $\beta_2$ agonists such as clenbuterol administered for the method of this invention are readily prepared by the skilled practitioner. Standard pharmaceutically acceptable inactive ingredients such as stabilizers, excipients, binding agents, carriers, vehicles, flavorants, preservatives may be part of the compositions. More than one $\beta_2$ agonist may be used in a given composition. Other active ingredients may also be included.

Among other active ingredients are $\beta_1$ antagonists and mixed $\beta$ blockers. Thus, also part of this invention is a pharmaceutical composition as described above which in addition to a $\beta_2$ agonist, includes one or more $\beta_1$ antagonists, or one or more a mixed $\beta$ blockers, or any combination of $\beta_1$ antagonists and mixed $\beta$ blockers. Both $\beta_1$ antagonists and mixed $\beta$ blockers are described above, and any compound possessing such activity may be used in this composition. Examples of $\beta_1$ antagonists are CGP 20712 A, atenolol, and metoprolol, while an example of a mixed $\beta$ blocker is propranolol. These compounds are present in the composition in an amount effective to prevent the known side effects of $\beta_2$ agonist administration caused by minor co-stimulation of the $\beta_1$ receptor, such as increased heartrate and blood pressure. This composition may include any one or more of the $\beta_2$ agonists of this invention. In particular this composition may include clenbuterol. A preferred composition includes clenbuterol and propranolol.

A further object of this invention is a method where one or both of a $\beta_1$ antagonist or a mixed $\beta$ blocker is additionally administered in an amount effective to reduce side effects caused by minor co-stimulation of the $\beta_1$ receptor by the $\beta_2$- agonist. "Reduce" has the meaning defined above, and specifics of administration may also be achieved as described above. The effective amount may be determined empirically by normalizing of racing heart, blood pressure, and other indicators of $\beta_1$ stimulation. If propranolol is used, a good starting dose is 20 mg/kg/day, or about 80 to about 640 mg/day. With regard to atenolol and metoprolol, about 50 to about 100 mg/day may be administered.

$\beta_2$ agonist pharmaceutical compositions of this invention may be administered in standard formulations known to a skilled practitioner or simply added to a chemically appropriate beverage such as water. For example, oral formulations such as tablets, syrups, etc. may be used. Subdermal implants or patches are also useful. Injectable solutions for injection into blood vessels, muscle, under the skin, etc. may also be used.

Dosage regimens will depend on the individual patient as monitored by the practitioner. The desired amount of $\beta_2$ agonist may be given in a single dose or in several doses over a specific time period. Thus a 40 $\mu$g dose could be provided in the form of two 20 $\mu$g doses over a 24 hour time period.

Treatment regimens may be continued for as long as required. In general $\beta_2$ agonists will be administered for one day to four weeks, depending on the patient's condition. However, a $\beta_2$ agonist may be administered indefinitely on a maintenance basis. $\beta_2$ agonists may also be provided on an intermittent basis to minimize receptor desensitization which may occur as a result of continued stimulation. For example, the selected dosage may be provided on a "two days on, three days off" type of schedule. In all these cases, a skilled practitioner will know how to adjust the dosages accordingly if necessary, based on improvements in the patient's condition, or evidence of desensitization (decreasing responsiveness to a previously effective dosage). $\beta_2$ agonists may also be administered prophylactically, for example in the case of spinal cord injury before scoliosis has a chance to develop.

The example which follows is illustrative and should not be construed to limit the invention in any way. Those of skill in the art will appreciate that there are a variety of other embodiments which are well within the scope of the present invention.

EXAMPLE 1

Treatment of Scoliosis in Animal Model

Methods:

The spinal cords of female Wistar rats (Charles River) were three-quarter transected at either T5 or T11 using methods similar to those of Little and coworkers (Little 1988).

All of the procedures involving vertebrate animals were approved by the Institutional Animal Care and Use Committee of New York Medical College.

Prior to surgery, anesthesia was induced with an injection of sodium pentobarbital (60 mg/kg ip) and laminectomy was performed at either T4–T5 or T10–T11 to expose the spinal cord. The cord was completely penetrated with a scalpel blade (No. 11) midway on the left side and drawn to the right, so that one-quarter of the total width remained intact. This procedure was repeated in order to remove a small wedge of cord tissue followed by closure of the incision with wound clips.

For some rats which served as sham-operated controls, laminectomy was performed at T4–T5 and the dura matter, but not the cord, was penetrated.

Some groups of T5 and T11 transected rats received clenbuterol (Chinoin Productos Pharmaceuticos, S.A. de CZ, Lago Tanganica Num. 18, Col. Granada del Miguel Hidalgo, 11520 Mexico d.f.). that was administered by adding it to the drinking water at a dose of 9 mg/L which supramaximally stimulates muscle growth. This dose is about equivalent to providing a human patient with 1000 μg/kg/day.

In all, 6 treatment groups were examined 4 weeks following surgery which had the following respective initial and final body weights ($\pm$SE): untreated, 166$\pm$4 and 246$\pm$10 (n=7), laminectomy, 167$\pm$4 and 268$\pm$8 (n=7), transection at T5, 188$\pm$2 and 214$\pm$7 (n=8), transection at T5 with clenbuterol treatment, 190$\pm$3 and 266$\pm$8 (n=6), transection at T11, 191$\pm$2 and 202$\pm$8 (n=9), transection at T11 with clenbuterol treatment, 190$\pm$2 and 246$\pm$10 (n=8).

The animals were anesthetized with isofluorane to relax the musculature and the paws were taped to the film cassette to maintain the prone position during x-ray exposure.

The mean positions of the centers of vertebrae T1–L6 relative to T1 and a midline between T1 and L6 were obtained from radiograms using a computerized digitizing tablet (Sigmascan)

Results:.

An animal model of spinal cord injury was used to produce neuromuscular scoliosis for treatment with clenbuterol. This model uses an asymmetric injury to the spinal cord and thus is a valid model for scoliosis, which has been shown to result from a variety of procedures including lesioning of the dorsal columns or posterior horn (Barrios 1987, Pincott I 1982) and either the posterior or anterior roots of the spinal cord (Suk 1989, Pincott II 1984). In the present experiments, rat spinal cords were sectioned three-quarters of the way through, beginning on the right side, so that the left lateral columns remained intact (see Methods above).

Because the transection is laterally asymmetrical, the unequal loading and lateral displacement of the vertebrae should result in scoliosis that is convex on the weakened side, as in other experiments involving neurological damage (Barrios 1987, Pincott I 1982, Suk 1989, Pincott II 1984). To detect lateral curvature of the spine, dorsal-ventral radiograms were obtained from groups of rats 4 weeks after transection at either T5 to T11 (see Methods above). In addition, identically transected rats, that received clenbuterol administered in the drinking water for 4 weeks, were also examined (see Methods above).

Subtotal transection at both T5 and T11 caused spinal curvature. Radiograms of thoracic and lumbar curves due to three-quarter transection at T5 and T11, respectively, are shown in FIG. 2. To determine which vertebrae were consistently affected by transection of the spinal cord, the mean lateral deviations of each vertebra from T1 to L6, relative to the rostral-caudal axis, were obtained for each treatment group (see Methods above). Significant lateral displacement to the right of the mean positions of vertebrae T9–T12 or of vertebrae L2–L5 of up to 4.5 mm were observed in response to subtotal transection at T5 or T11, respectively (FIG. 1).

The spinal curvature exhibited a range of severity ($\leq$11 mm) and in a few cases in each group, curvature was not apparent. This differential responsiveness to three-quarter transection is consistent with the previous finding that locomotor deficits also show a range of severity (Little 1988). Previously, Little and coworkers found that there is some recovery from the paralysis that results from three-quarter transection, which occurs gradually over a period of 4 weeks (Little 1988). The return of locomotor function exhibited some variability which correlated with the amount of cord that remained intact at the level of section. Hemisection was not performed in the present experiments, since recovery is very rapid. In contrast to the results with partial transection, groups of rats that were unoperated or received laminectomy alone did not exhibit scoliosis (see Methods above, FIG. 1). In order to perform laminectomy, section of paraspinal muscles is also required, but neither of these operations was sufficient to cause spinal curvature.

As expected from previous studies, three-quarter transection at the levels of either T5 or T11 produced curves that are convex toward the side that was completely sectioned. In addition, the resulting curves are located in positions that correspond to the level of section. Thus, transection at T5 or T11 resulted in thoracic and lumbar curves, respectively, that were distal to the site of injury. The number of vertebrae between the lesion site and the apex of the resulting curve was 5 after section at T5 (apex at T11) and 4 after section at T11 (apex at L3). This result appears to be related to the anatomical finding that the innervation for paraspinal muscles arises proximally from the spinal cord at the level of the tendon origins (Macintosh 1986). Therefore, spinal cord injury that causes weakness may be expected to affect the loading of more distal vertebrae. However, because the vertebral column is supported by a variety of muscles, the extent to which each muscle contributes to the generation of a given curve is not known with certainty.

Figure 1:
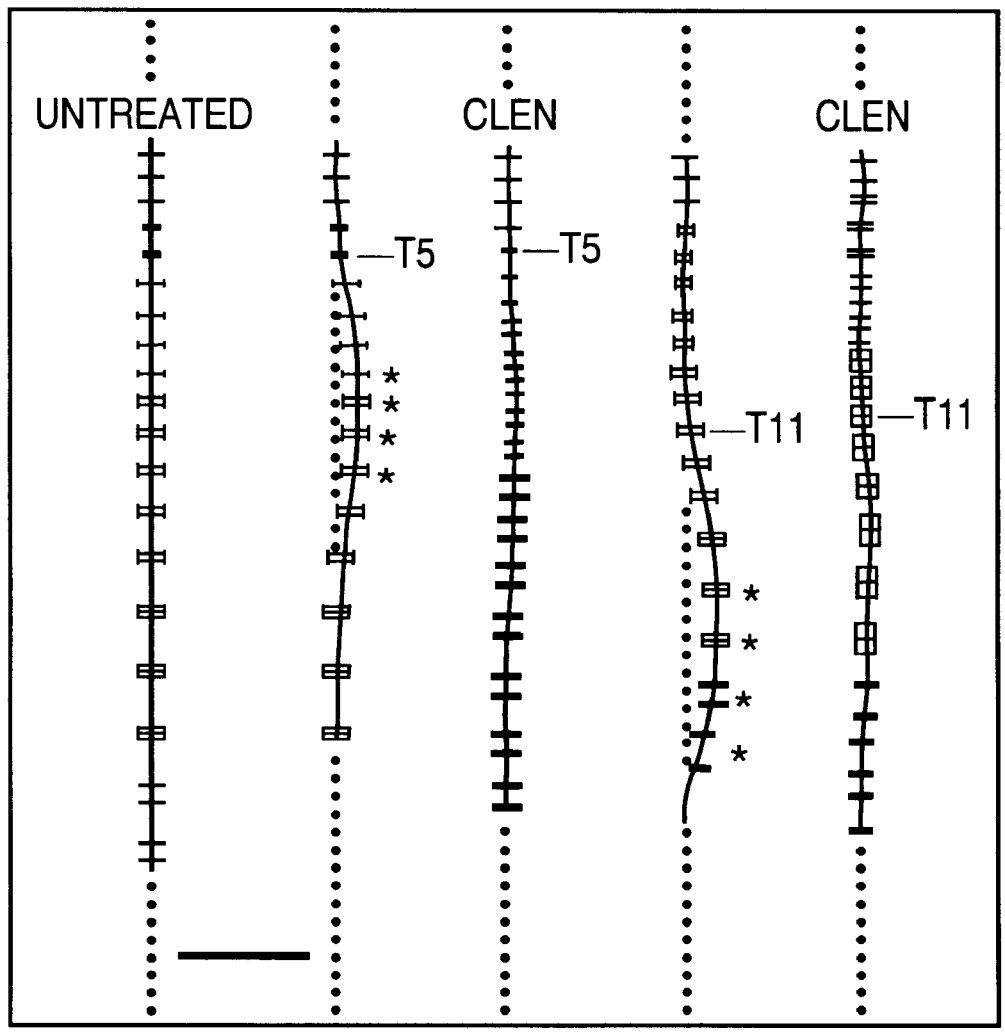
FIG. 1. Plots of the mean rostral-caudal and lateral positions of the centers of vertebrae T1–L6 (±SE) relative to T1 and a midline between T1 and L6. The results shown are from 5 treatment groups that were (left to right) untreated, three-quarter transected at T5, three-quarter transected at T5 with clenbuterol treatment, three-quarter transected at T11 and three-quarter transected at T11 with clenbuterol treatment. Plots of the vertebral positions of rats receiving laminectomy alone were similar to the untreated group. The horizontal bar at the bottom left indicates a length of two centimeters. *p<0.05, significant lateral deviation compared to groups that were untreated or received laminectomy alone, Duncan's test (SPSS).
Figure 2A:
FIG. 2. Dorsoventral radiograms of rats showing thoracic scoliosis 4 weeks after three-fourths spinal cord transection at T5 (1st panel on the left) or lumbar scoliosis after three-fourths transection at T11 (3rd panel). Radiograms shown in 2nd and 4th panels demonstrate that scoliosis is greatly reduced by clenbuterol after three-fourths transection at T5 and T11, respectively.
Figure 2B:
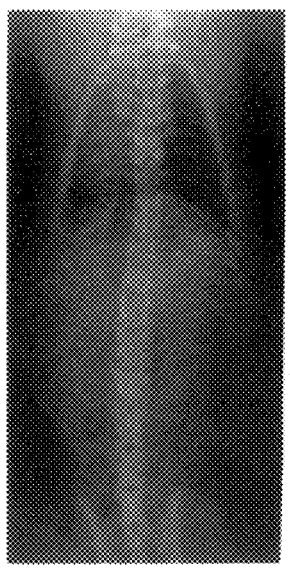
Figure 2C:
Figure 2D:
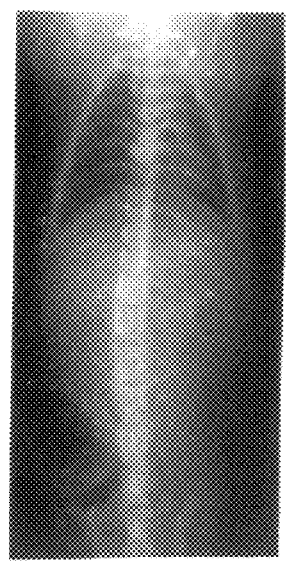

Unexpectedly, significant lateral displacement of the vertebrae was absent in groups of rats that were treated with clenbuterol for 4 weeks following identical three-quarter transection of the spinal cord at T5 or T11 (FIG. 1). The mechanism for this result is unknown, as was its existence prior to this work.

References

1. W. W. Dearolf III et al., *J. Pediatr. Orthop.* 10, 214 (1990).
2. R. D. D'Ambrosia, Ed., *Musculoskeletal Disorders: Regional Examination and Differential Diagnosis* (J. B. Lippincott Company, Philadelphia, Pa., 1986).
3. C. S. B. Galasko and C. M. Delaney, *Muscle & Nerve* 16, 433 (1933).
4. R. K. Beals, *Clinical Orthop. Rel. Res.* 93, 23 (1973).
5. A. Schultz, K. Haderspeck, S. Takashima, *Spine* 6, 468 (1981).
6. S. T. Takashima, S. P. Singh, K. A. Haderspeck, A. B. Schultz, *J. Biomechanics* 12, 929 (1979).
7. D. N. Ghista et al., *J. Biomechanics* 21, 77 (1988).
8. J. Maguire, R. Madigan, S. Wallace, R. Leppanen, V. Draper, *Spine* 18, 1621 (1993).
9. K. P. Kennelly and M. J. Stokes, *Spine* 18, 913 (1993).
10. R. J. Zeman, R. Ludemann, J. D. Etlinger, *Am. J. Physiol.* 252 (Endocrinol. Metab. 15), E152 (1987). Zeman I
11. R. J. Zeman, A. Hirschman, M. L. Hirschman, G. Guo, J. D. Etlinger, *Am. J. Physiol.* 261 (Endocrinol. Metab. 24), E285 (1991). Zeman II 12. E. T. Agbenyega and A. C. Wareham, *Muscle & Nerve* 13, 199 (1990).
13. R. J. Zeman, Y. Zhang, J. D. Etlinger, *Am. J. Physiol.* 267 (Cell Physiol. 36):C865 (1994). Zeman III
14. J. W. Little, R. M. Harris, R. C. Sohlberg, *Neuroscience Letters* 87, 189 (1988).
15. C.Barrios, M. T. Tunon, J. A. DeSalis, J. L. Beguiristain and J. Canadell, *Spine* 12, 433 (1987).
16. J. R. Pincott and L. F. Taffs, *J. Bone Joint Surg.* 64B, 503 (1982). Pincott I
17. S. I. Suk, H. S. Song, C. K. Lee, *Spine* 14, 692 (1989).
18. J. R. Pincott, J. S. Davies, L. F. Taffs, *J. Bone Joint Surg.* 66B, 27 (1984). Pincott II
19. P. J. Reeds, S. M. Hay, P. M. Dorwood, R. M. Palmer, *Br. J. Nutrition* 56, 249 (1986).
20. J. E. Macintosh, F. Valencia, N. Bogduk, R. R. Munro, *Clin. Biomech.* 1, 196 (1986).
21. J. H. Williams and W. S. Barnes, *Muscle & Nerve* 12, 968 (1989).
22. W. C. Bowman, in *Handbook of Experimental Pharmacology*, L. Serkeres, Ed. (Springer Verlag, Berlin, Heidelberg, 1980), vol. 54/II.
23. R. J. Zeman, R. Ludemann, T. G. Easton, J. D. Etlinger, *Am J. Physiol.* 254 (Endocrinol. Metab. 17), E726 (1988). Zeman IV
24. P. Follesa and I. Mocchetti, *Molec. Pharmac.* 43, 132 (1992).
25. T. Kasamatsu and T. Shirokawa, *Exp. Brain Res.* 59, 507 (1985).
26. J. Kwon, S. Farrell, M. Downen, E. Eves, B. H. Wainer, paper presented at the 24th Annual Meeting of the Society for Neuroscience, Miami Beach, Fla., Nov. 14, 1994.
27. E. Zaimis, *The Lancet* 1(800), 403 (1973).
28. C. A. Maltin, M. I. Delday, J. S. Watson, S. D. Heys, I. M. Nevison, I. K. Ritchie, P. H. Gibson, *Clinical Science* 84, 651 (1993).
29. M. N. Sillence et al., *Amer. J. Physiology* 268, E158 (1995).

We claim:

1. A method for treating scoliosis which comprises administering to a patient with scoliosis at least one $\beta_2$-adrenergic agonist selected from the group consisting of clenbuterol, albuterol, salmeterol, ractopamine, salbutamol, cimaterol, BRL-47672, terbutaline, fenoterol, metaproterenol, isopraline, MJ-9184-1, trimetoquinol, tetrahydropapaveroline, soterenol, salmefarnol, rimiterol, QH-25, isoetharine, R-804, orciprenaline, quinterenol, sulfonterol, dobutamine, and isoproterenol and salts of the foregoing in an amount effective to reduce the scoliosis.

2. A method according to claim 1 which comprises additionally administering one or both of 1) a $\beta_2$-antagonist selected from the group consisting of CgP 20712, atenolol and metaprolol; and 2) propranolol, in an amount effective to reduce side effects caused by stimulation of the $\beta_1$ receptor.

3. A method according to claim 2 wherein said $\beta_2$ adrenergic agonist is used in an amount of from about 0.5 to about 1000 $\mu$g/kg/day.

4. A method according to claim 2 wherein said $\beta_1$-antagonist is used in an amount of from about 80 to about 640 mg/kg/day and said propranolol is used in an amount of from about 80 to about 640 mg/kg/day.

5. A method according to claim 2 wherein said $\beta_2$-adrenergic agonist is clenbuterol, and said $\beta_1$-antagonist is a member selected from the group consisting of atenolol and metaprolol.

6. The method of claim 2 wherein the effective amount of propranolol is from about 80 to about 640 mg/kg.

7. The method of claim 2 wherein the $\beta_1$ antagonist is selected from the group consisting of atenolol and metoprolol.

8. The method of claim 5 wherein the effective amount of atenolol or metoprolol is from about 50 to about 100 mg/kg/day.

9. The method of claim 1 wherein the $\beta_2$ adrenergic agonist is selected from the group consisting of clenbuterol, albuterol, salmeterol, ractopamine, salbutamol, cimaterol, BRL-47672, terbutaline, fenoterol, metaproterenol, and isopraline and salts of the foregoing.

10. The method of claim 1 wherein the $\beta_2$ adrenergic agonist is clenbuterol.

11. The method of claim 10 wherein the effective amount of clenbuterol is from about 10.0 to about 100.0 $\mu$g/kg/day.

12. The method of claim 11 wherein the effective amount of clenbuterol is about 40 $\mu$g/kg/day.

* * * * *